US012683028B2

(12) United States Patent　　(10) Patent No.:　US 12,683,028 B2
Luo et al.　　　　　　　　　　　　(45) Date of Patent:　　Jul. 14, 2026

(54) ELECTROCARDIOGRAM-BASED DIAGNOSIS MODEL LEARNING DEVICE, ELECTROCARDIOGRAM-BASED DIAGNOSIS MODEL LEARNING METHOD, AND STORAGE MEDIUM

(71) Applicant: NEC Corporation, Tokyo (JP)

(72) Inventors: Yuan Luo, Tokyo (JP); Mitsuru Noma, Tokyo (JP); Osamu Hisamatsu, Tokyo (JP); Kosuke Nishihara, Tokyo (JP); Masahiro Kubo, Tokyo (JP); Hiroaki Kataoka, Tokyo (JP); Akihiko Shibano, Tokyo (JP)

(73) Assignee: NEC CORPORATION, Tokyo (JP)

( * ) Notice: Subject to any disclaimer, the term of this patent is extended or adjusted under 35 U.S.C. 154(b) by 114 days.

(21) Appl. No.: 18/480,042

(22) Filed: Oct. 3, 2023

(65) Prior Publication Data

US 2024/0161925 A1　　May 16, 2024

(30) Foreign Application Priority Data

Nov. 16, 2022　(JP) ................................. 2022-183080

(51) Int. Cl.
*G16H 50/20*　　　(2018.01)
*A61B 5/00*　　　(2006.01)
*A61B 5/318*　　　(2021.01)

(52) U.S. Cl.
CPC ............. *G16H 50/20* (2018.01); *A61B 5/318* (2021.01); *A61B 5/7221* (2013.01); *A61B 5/742* (2013.01)

(58) Field of Classification Search
CPC ........ G16H 50/20; G16H 50/70; A61B 5/318; A61B 5/7221; A61B 5/742; A61B 5/346; A61B 5/7267
See application file for complete search history.

(56) References Cited

U.S. PATENT DOCUMENTS

2020/0260979 A1* 8/2020 Cao ......................... A61B 5/366
2022/0130548 A1* 4/2022 Tamura .................. G16H 50/20

FOREIGN PATENT DOCUMENTS

WO　　WO-2020004369 A1 * 1/2020 .............. G06T 7/00
WO　　2022/064708 A1　　3/2022

* cited by examiner

*Primary Examiner* — Chinyere Mpamugo
(74) *Attorney, Agent, or Firm* — Sughrue Mion, PLLC

(57)　　　　　ABSTRACT

A learning device 1X mainly includes a first acquisition means 31X, a second acquisition means 32X, and a learning means 34X. The first acquisition means 31X acquires a partial waveform of electrocardiogram data regarding an electrocardiogram of a subject. The second acquisition means 32X acquires an attention interval, which is used as a basis for a diagnosis of a target disease, in a sequential waveform of the electrocardiogram data. The learning means 34X trains a model configured to diagnose the target disease, based on the partial waveform and the attention interval.

8 Claims, 11 Drawing Sheets

FIG. 1

INTERFACE  11

PROCESSOR  13

INPUT UNIT  14

OUTPUT UNIT  15

MEMORY

MODEL STORAGE UNIT  21

TRAINING DATA STORAGE UNIT  22

12

19

1

12 LEADS
IN TOTAL

I LEAD

II LEAD

III LEAD aVR LEAD

V1 LEAD

SELECT IN ACCORDANCE WITH
TARGET DISEASE

SELECTED
3 LEADS

I LEAD

II LEAD

VI LEAD

FIG. 4

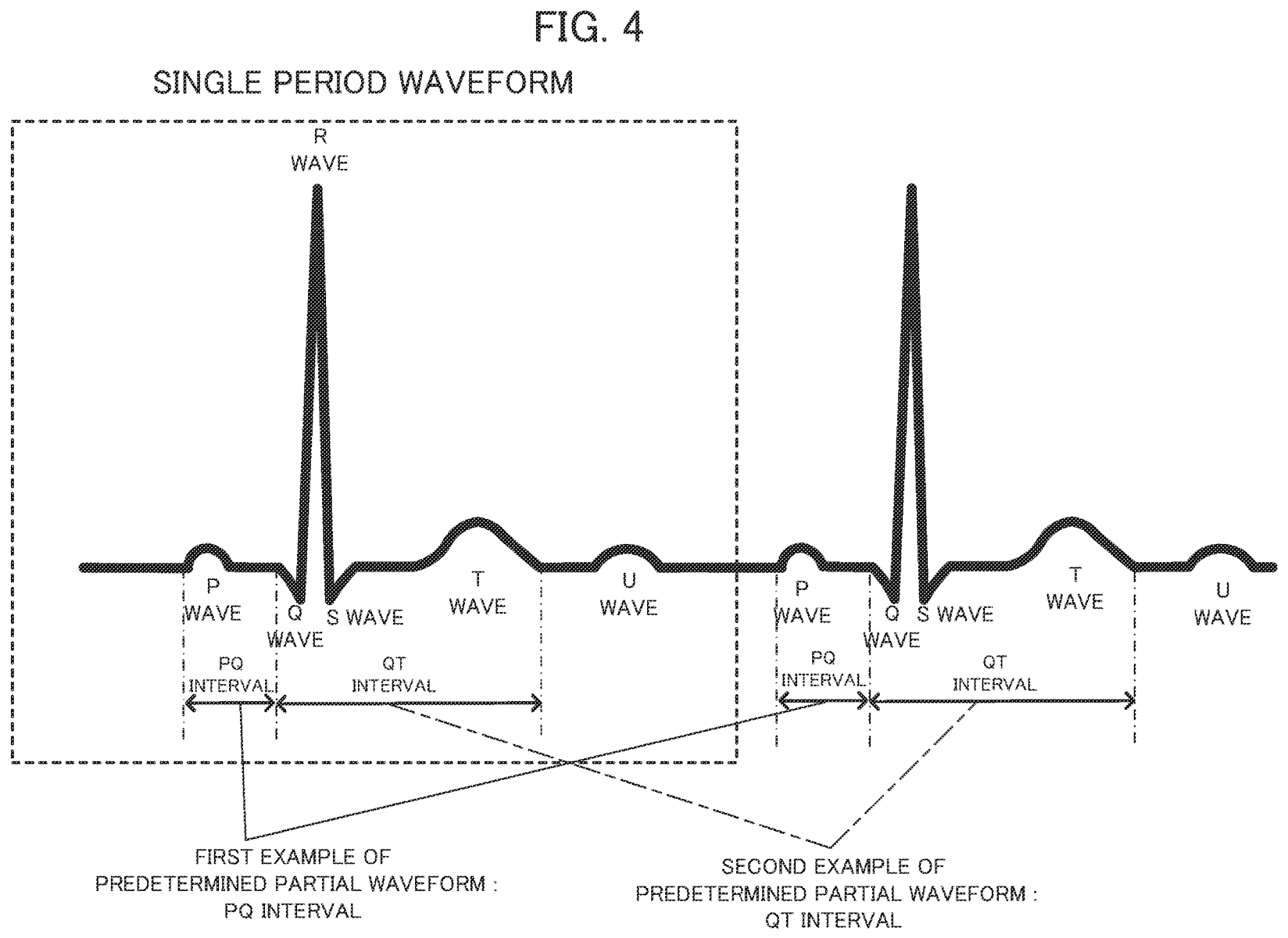

SINGLE PERIOD WAVEFORM

R WAVE

P WAVE

PQ INTERVAL

Q WAVE

S WAVE

QT INTERVAL

T WAVE

U WAVE

P WAVE

PQ INTERVAL

Q WAVE

S WAVE

QT INTERVAL

T WAVE

U WAVE

FIRST EXAMPLE OF PREDETERMINED PARTIAL WAVEFORM : PQ INTERVAL

SECOND EXAMPLE OF PREDETERMINED PARTIAL WAVEFORM : QT INTERVAL

FIG. 9

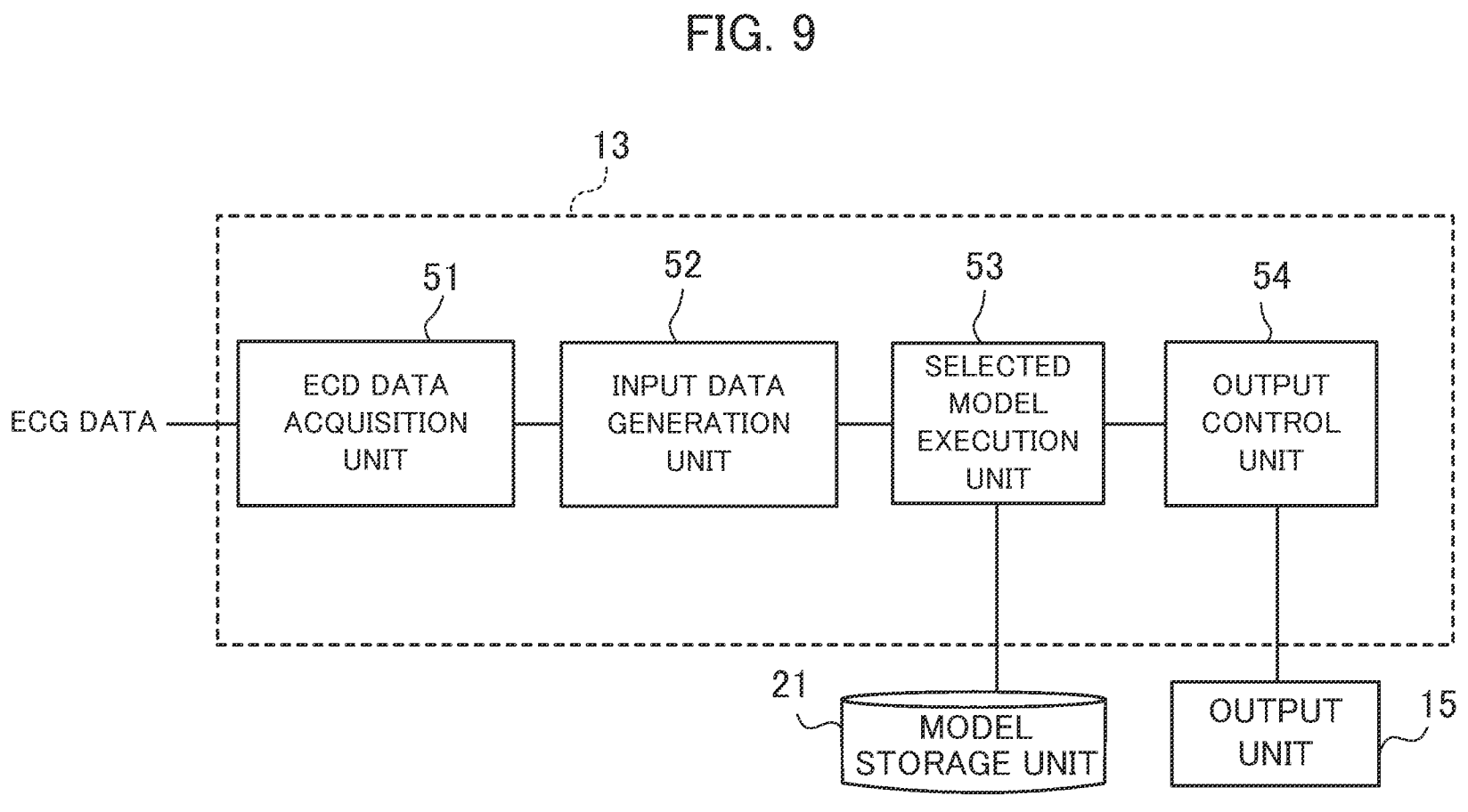

ECG DATA

51 — ECG DATA ACQUISITION UNIT

52 — INPUT DATA GENERATION UNIT

53 — SELECTED MODEL EXECUTION UNIT

54 — OUTPUT CONTROL UNIT

13

21 — MODEL STORAGE UNIT

15 — OUTPUT UNIT

ELECTROCARDIOGRAM-BASED DIAGNOSIS MODEL LEARNING DEVICE, ELECTROCARDIOGRAM-BASED DIAGNOSIS MODEL LEARNING METHOD, AND STORAGE MEDIUM

INCORPORATION BY REFERENCE

This application is based upon and claims the benefit of priority from Japanese Patent Application No. 2022-183080, filed on Nov. 16, 2022, the disclosure of which is incorporated herein in its entirety by reference.

TECHNICAL FIELD

The present disclosure relates to a technical field of a learning device, a learning method, and a storage medium for learning of a model configured to diagnose a disease based on an electrocardiogram.

BACKGROUND

There is a device configured to determine the presence or absence of a disorder of a subject by analyzing the measured electrocardiogram of the subject. For example, Patent Literature 1 discloses a technique relating to learning and utilization of a disease estimation model configured to estimate a possibility of a disease using the electrocardiogram waveform measured from a subject.

CITATION LIST

Patent Literature

Patent Literature 1: WO2022/064708

SUMMARY

In the diagnosis regarding the existence of a disease based on an electrocardiogram, since a waveform part to be noticed according to the disease is predetermined based on experimental knowledge, a doctor or a computer determines the existence of the disease by observing the waveform part. On the other hand, unfortunately, there could occur an important change in a part other than the above-described waveform part to be observed to determine the existence of the disease, and the doctor or the computer could overlook such a change.

In view of the above-described issues, one object of the present disclosure is to provide a learning device, a learning method, and a storage medium capable of performing learning regarding a model configured to diagnose diseases based on an electrocardiogram.

In an example aspect of the present disclosure, there is provided a learning device including:

a first acquisition means configured to acquire a partial waveform of electrocardiogram data regarding an electrocardiogram of a subject;

a second acquisition means configured to acquire an attention interval, which is used as a basis for a diagnosis of a target disease, in a sequential waveform of the electrocardiogram data; and a learning means configured to perform a learning of a model configured to diagnose the target disease, based on the partial waveform and the attention interval.

In an example aspect of the present disclosure, there is provided a learning method executed by a computer, the learning method including:

acquiring a partial waveform of electrocardiogram data regarding an electrocardiogram of a subject;

acquiring an attention interval, which is used as a basis for a diagnosis of a target disease, in a sequential waveform of the electrocardiogram data; and performing a learning of a model configured to diagnose the target disease, based on the partial waveform and the attention interval.

In an example aspect of the present disclosure, there is provided a non-transitory computer readable storage medium storing a program executed by a computer, the program causing the computer to:

acquire a partial waveform of electrocardiogram data regarding an electrocardiogram of a subject;

acquire an attention interval, which is used as a basis for a diagnosis of a target disease, in a sequential waveform of the electrocardiogram data; and perform a learning of a model configured to diagnose the target disease, based on the partial waveform and the attention interval.

An example advantage according to the present disclosure is to accurately perform learning regarding a model configured to diagnose a disease based on an electrocardiogram.

BRIEF DESCRIPTION OF THE DRAWINGS

FIG. 1 illustrates an example of a hardware configuration of a learning device common to each example embodiment.

FIG. 4 illustrates an enlarged view of a waveform of lead data.

FIG. 9 is a functional block diagram of the learning device 1 according to the third example embodiment.

EXAMPLE EMBODIMENTS

Figure 2:
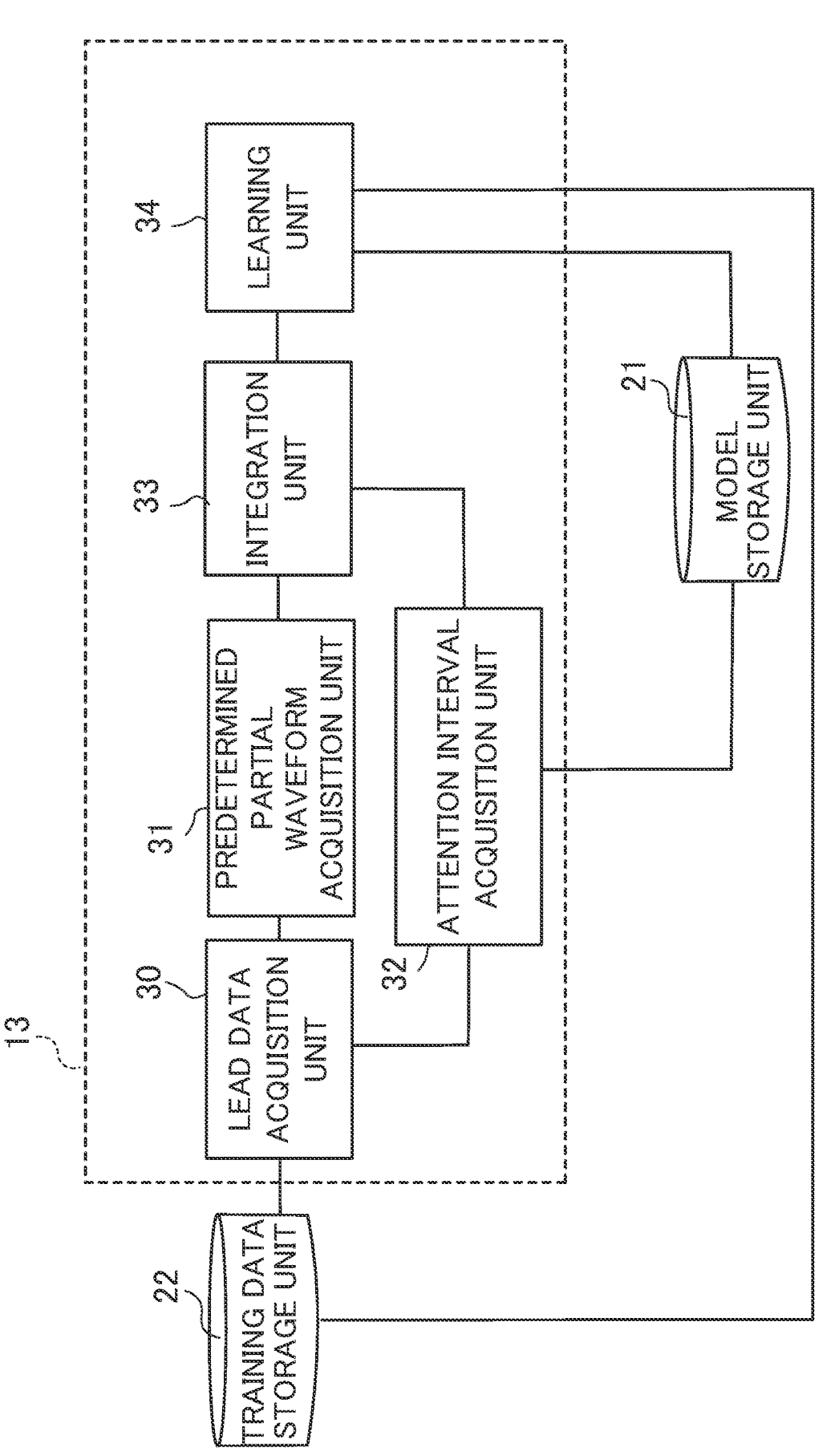
FIG. 2 is a functional block diagram of a learning device in the first example embodiment.

Hereinafter, example embodiments of an electrocardiogram-based diagnosis model learning device, an electrocardiogram-based diagnosis model learning method, and a storage medium will be described with reference to the drawings.

First Example Embodiment

(1) System Configuration

Figure 1:
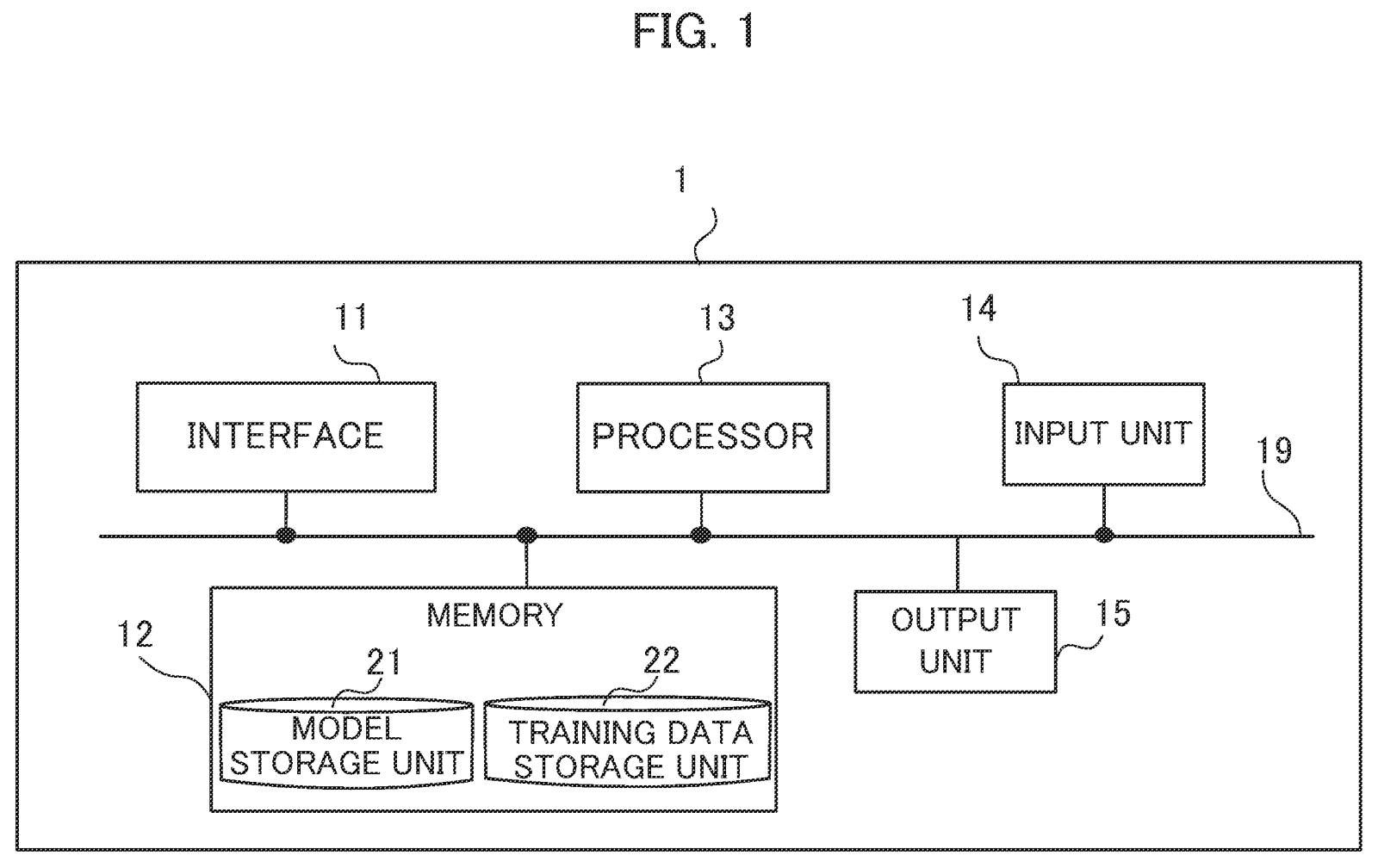

FIG. 1 shows an example of a hardware configuration of the learning device 1. The learning device 1 performs a learning of a model configured to make a determination regarding one or more diseases (also referred to as "target disease") to be diagnosed on the basis of ECG data which is data relating to an electrocardiogram of a subject. The learning device 1 mainly includes an interface 11, a memory 12, a processor 13, an input unit 14, and an output unit 15. Each of these elements is connected to one another via a data bus 19. The target disease is mainly assumed herein to be a circulatory disease, but may be any disease detectable by electrocardiogram analysis.

The interface 11 performs interface operation between the learning device 1 and an external device. In this instance, examples of the interface 11 include a communication interface, such as a network adapter, for communicating wirelessly or wirelessly with an external device that is a separate device from the learning device 1, and a hardware interface which conforms to a USB (Universal Serial Bus), a SATA (Serial AT Attachment), or the like.

The memory 12 is configured by non-volatile and volatile memories to be used as working memories and/or for storing information for processing by the learning device 1, such as a RAM (Random Access Memory) and a ROM (Read Only Memory). The memory 12 may include an external storage device, such as a hard disk, that is connected or embedded in the learning device 1, or may include a storage medium, such as a removable flash memory. The memory 12 stores a program for the learning device 1 to execute each processing according to the present example embodiment.

The memory 12 functionally includes a model storage unit 21 and a training data storage unit 22.

The model storage unit 21 stores the parameters of the model configured to output the evaluation result (i.e., diagnosis result) indicating the presence or absence of the target disease based on ECG data. The ECG data herein indicates lead data representing each lead of the twelve-lead electrocardiogram obtained by a test for recording the electrical activity and change in the heart from ten electrodes in total attached to six points of the chest, both wrists, and both ankles. The types (which may be one or more types selected from twelve leads) of the leads to be used as the lead data to determine the presence or absence of the target disease vary depending on the target disease.

For example, the model is a machine learning model such as a neural network or a support vector machine, and it is trained in advance to output an evaluation result of the presence or absence of the target disease when the lead data is inputted to the model. The learned parameters thereof are stored in the model storage unit 21. When the model is configured by a neural network, the model storage unit 21 stores various parameters regarding the neural network such as a layer structure, a neuron structure of each layer, the number of filters and the size of filters in each layer, and the weight for each element of each filter, for example.

In the present example embodiment, the parameters of each of a first model, a second model, and a third model (machine learning model) are stored in the model storage unit 21.

The first model is a model configured to output an inference result of the presence or absence of the target disease of a subject when lead data which is waveform data obtained by combining partial waveforms (also referred to as "predetermined partial waveforms") is inputted to the model, wherein each predetermined partial waveform is smaller than a single-period waveform and is predetermined to be effective in making a diagnosis of the target disease. The predetermined partial waveform is predetermined based on experimental knowledge and the like so as to be an appropriate interval (segment) depending on the target disease. The first model is, for example, a machine learning model, and is trained in advance using training data having a plurality of sets (records) of lead data equivalent to a predetermined partial waveform and the corresponding correct answer label indicating the presence or absence of the target disease of a subject, and the parameters of the learned first model are stored in the model storage unit 21.

The second model is a model configured to output, when data of the sequential waveform equivalent to whole lead data is inputted thereto, the presence of absence of the target disease of the subject and an interval (also referred to as "attention interval") in the sequential waveform, which is emphasized (i.e., used as the basis for diagnosis) in determining the existence of the target disease. When the second model is a convolutional neural network, the second model finally outputs the presence or absence of the target disease of the subject while generating information (also referred to as "attention interval information") indicating the attention interval as the output from the intermediate layer. In this case, for example, attention mechanism is added to the second model so that the output data in front of the full connection is inputted to the attention mechanism. Then, any interval whose corresponding coefficient outputted by the attention mechanism is equal to or more than a predetermined value is identified as an attention interval. In this case, the second model is trained in advance using training data having a plurality of sets of data of the sequential waveform and the corresponding correct answer label indicating the presence or absence of the target disease of the subject, and the parameters of the learned second model are stored in the model storage unit 21.

The third model is a machine learning model configured to output an inference result of presence or absence of the target disease of the subject when the lead data corresponding to both of the predetermined partial waveforms used for input to the first model and partial waveforms (also referred to as "regular partial waveforms") which regularly become attention intervals other than the predetermined partial waveforms. The regular partial waveform is, for example, a portion other than the predetermined partial waveforms where the attention interval periodically appears by a predetermined degree or more of frequency. For example, the regular partial waveform is a partial waveform which appears at least twice in five-period waveforms while the error of the relative distance to the nearest R-wave ranges from 0 to 0.1T. In the present example embodiment, the learning device 1 performs the learning of the third model using the attention intervals obtained by using the learned second model, and stores learned parameters of the third model obtained in the model storage unit 21. Before execution of the learning, for example, initial parameters of the third model are stored in the model storage unit 21.

Each of the above-described models may be a model that is trained to be specific to each possible disease that may be used as a target disease. In this case, in the model storage unit 21, the parameters of the model corresponding to each possible disease that may be used as a target disease are stored.

The training data storage unit 22 stores the training data (training data set) to be used for training the third model. The training data includes a plurality of sets of lead data of a subject that becomes a sample of input data prepared for training and the corresponding correct answer label indicating the presence or absence of the target disease of the subject.

The processor 13 executes a predetermined process by executing a program or the like stored in the memory 12. The processor 13 is a processor such as a CPU (Central Processing Unit), a GPU (Graphics Processing Unit), and a TPU (Tensor Processing Unit). The processor 13 may be configured by a plurality of processors. The processor 13 is an example of a computer.

The input unit 14 generates an input signal. Examples of the input unit 14 include a button, a touch panel, a remote controller, and a voice input device. The output 15 displays and/or outputs, by audio, information under the control of the processor 13. Examples of the output unit include a display, a projector, and a speaker. The output unit 15 is an example of a display device.

The configuration of the learning device 1 shown in FIG. 1 is an example, and various changes may be made thereto. For example, the ECG data may be pre-stored in the memory 12 instead of being supplied from an external device. In another example, at least one of the input unit 14 or the output unit 15 may be an external device connected to the learning device 1 via the interface 11 or the like. In yet another example, at least some information stored in the memory 12 may be stored in an external device connected to the learning device 1. In this case, the above-mentioned external device may be configured as one or more server devices.

(2) Functional Blocks

FIG. 2 is a functional block diagram of the learning device 1 relating to the learning of the third model. The processor 13 of the learning device 1 functionally includes a lead data acquisition unit 30, a predetermined partial waveform acquisition unit 31, an attention interval acquisition unit 32, an integration unit 33, and a learning unit 34 in relation to learning of the third model. Here, any blocks to exchange data with each other are connected to each other by a solid line, but the combination of the blocks to exchange data with each other is not limited to FIG. 2. The same applies to the drawings of other functional blocks described below.

The lead data acquisition unit 30 acquires the lead data to be used for training from the training data storage unit 22 through the interface 11. In this case, for example, the lead data acquisition unit 30 sequentially acquires the lead data of each set selected, in order, from the plurality of sets of lead data and the corresponding correct label stored in the training data storage unit 22, and supplies the acquired lead data to the predetermined partial waveform acquisition unit 31 and the attention interval acquisition unit 32. In this case, the lead data of each set is sequentially processed by the predetermined partial waveform acquisition unit 31, the attention interval acquisition unit 32, the integration unit 303, and the learning unit 34. When the twelve pieces of lead data corresponding to the twelve lead are stored in the training data storage unit 22, the lead data acquisition unit 30 acquires the lead data corresponding to leads predetermined as one or more leads suitable for the diagnosis of the target disease.

The predetermined partial waveform acquisition unit 31 extracts the lead data corresponding to the predetermined partial waveforms according to the target disease from the lead data supplied from the lead data acquisition unit 30, and supplies the extracted lead data to the integration unit 33. In this case, for example, if information indicating a waveform part to be extracted as the predetermined partial waveforms is stored in the memory 12 or the like, the predetermined partial waveform acquisition unit 31 extracts the lead data corresponding to the predetermined partial waveforms with reference to the information.

The attention interval acquisition unit 32 extracts the lead data corresponding to the attention intervals from the lead data supplied from the lead data acquisition unit 30 and supplies the extracted lead data to the integration unit 33. In this case, the attention interval acquisition unit 32 inputs the lead data corresponding to the sequential waveform to the second model built on the basis of the learned parameters of the second model stored in the model storage unit 21, and acquires the attention interval information outputted from the second model. In the case of using a plurality of leads, the attention interval acquisition unit 32 inputs the lead data of each lead to the second model in order, and acquires the attention interval information outputted from the second model for each lead. The attention interval acquisition unit 32 supplies the attention interval information and the lead data corresponding to the attention intervals to the integration unit 33.

It is noted that, in such a case that the determination result of the target disease by the second model is incorrect, the reliability is also low for the attention intervals outputted by the second model, and therefore, training the third model based on such attention intervals could cause the deterioration of the accuracy of the learned third model. Taking the above into consideration, the learning device 1 may perform processing by the integration unit 33 and the learning unit 34 only when the determination result of the presence or absence of the target disease outputted by the second model coincides with the presence or absence of the target disease indicated by the correct answer label corresponding to the lead data inputted to the second model. In other words, the learning device 1 does not update the parameters of the third model based on the lead data when the presence or absence of the target disease indicated by the correct answer label corresponding to the lead data inputted to the second model is not identical to the determination result of the presence or absence of the target disease outputted by the second model. This makes it possible to acquire the learned third model with high accuracy.

The integration unit 33 generates the lead data to be inputted to the third model, based on the lead data corresponding to the predetermined partial waveforms supplied from the predetermined partial waveform acquisition unit 31 and the lead data corresponding to the attention intervals supplied from the attention interval acquisition unit 32. In this case, the integration unit 33 identifies the regular partial waveforms based on the attention intervals indicated by the attention interval information supplied from the attention interval acquisition unit 32, and generates the lead data into which the lead data corresponding to the predetermined partial waveforms and the lead data corresponding to the regular partial waveforms are integrated (merged), as the lead data to be inputted to the third model. The approach for identifying the regular partial waveforms from the attention intervals may be based on an arbitrary pattern recognition technique. The integration unit 33 may display the sequential waveform of the lead data with clear indication of the attention intervals on the output unit 15 and identify the partial waveform specified by the user by the input unit 14 in the displayed sequential waveform as the regular partial waveforms. The integration unit 33 supplies the generated lead data for input to the third model to the learning unit 34.

The learning unit 34 trains the third model based on the lead data supplied from the integration unit 33 and the correct answer label stored in the training data storage unit 22. In this case, for example, the learning unit 34 determines the parameters of the third model such that the error (loss) between the determination result of the presence or absence of the target disease outputted by the third model when the lead data supplied from the integration unit 33 is inputted to the third model and the presence or absence of the target disease indicated by the correct answer label associated with the lead data acquired by the lead data acquisition unit 30 is minimized. The algorithm for determining parameters to minimize the loss may be any learning algorithm used in machine learning, such as the gradient descent and the error back propagation method. Then, the learning unit 34 updates the above-described parameters for each set selected from the plurality of sets of the lead data and the correct answer label stored in the training data storage unit 22, and stores the parameters of the updated third model in the predetermined partial waveform acquisition unit 31. In such a case that plural leads are used for diagnosis of the target disease, for example, the learning unit 34 may input these plural lead data as one input data (data in a predetermined tensor format) to the third model by stacking the plural lead data in the channel direction.

Here, for example, each component of the lead data acquisition unit 30, the predetermined partial waveform acquisition unit 31, the attention interval acquisition unit 32, the integration unit 33, and the learning unit 34 described in FIG. 2 can be realized by the processor 13 executing a program. In addition, the necessary program may be recorded in any non-volatile storage medium and installed as necessary to realize the respective components. In addition, at least a part of these components is not limited to being realized by a software program and may be realized by any combination of hardware, firmware, and software. At least some of these components may also be implemented using user-programmable integrated circuitry, such as FPGA (Field-Programmable Gate Array) and microcontrollers. In this case, the integrated circuit may be used to realize a program for configuring each of the above-described components. Further, at least a part of the components may be configured by a ASSP (Application Specific Standard Produce), ASIC (Application Specific Integrated Circuit) and/or a quantum processor (quantum computer control chip). In this way, each component may be implemented by a variety of hardware. The above is true for other example embodiments to be described later. Further, each of these components may be realized by the collaboration of a plurality of computers, for example, using cloud computing technology.

(3) Specific Example

Figure 3:
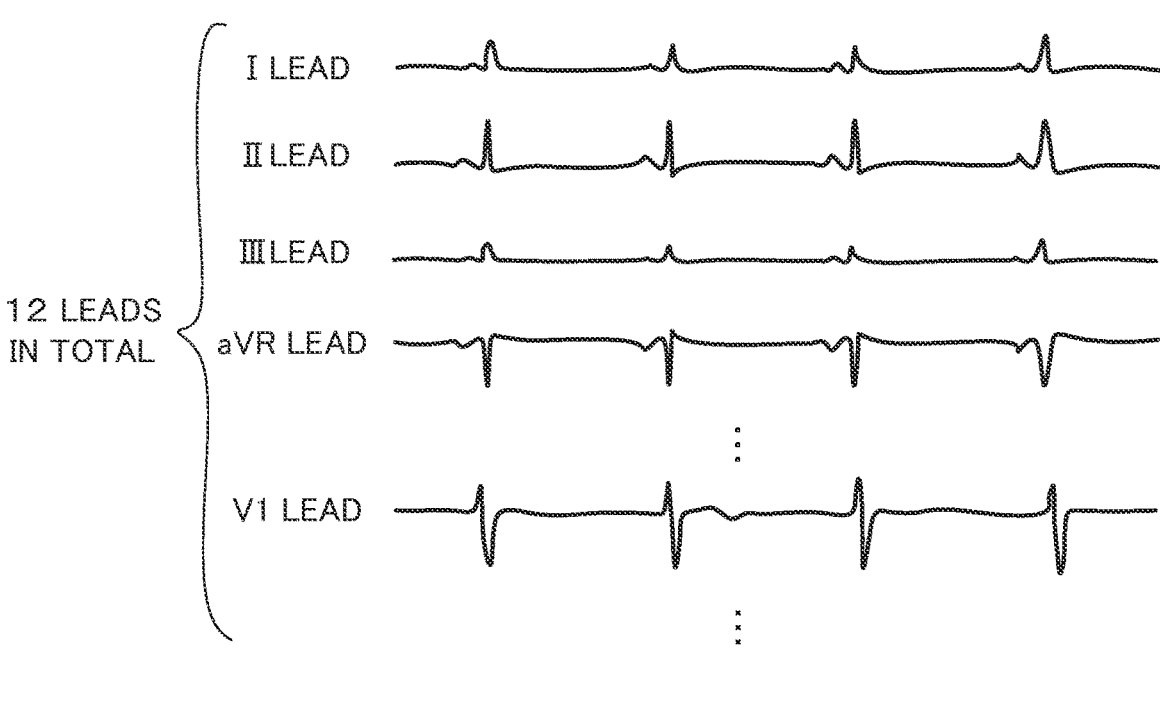
FIG. 3 illustrates the lead data selected when the target disease is atrial fibrillation.
Figure 3:
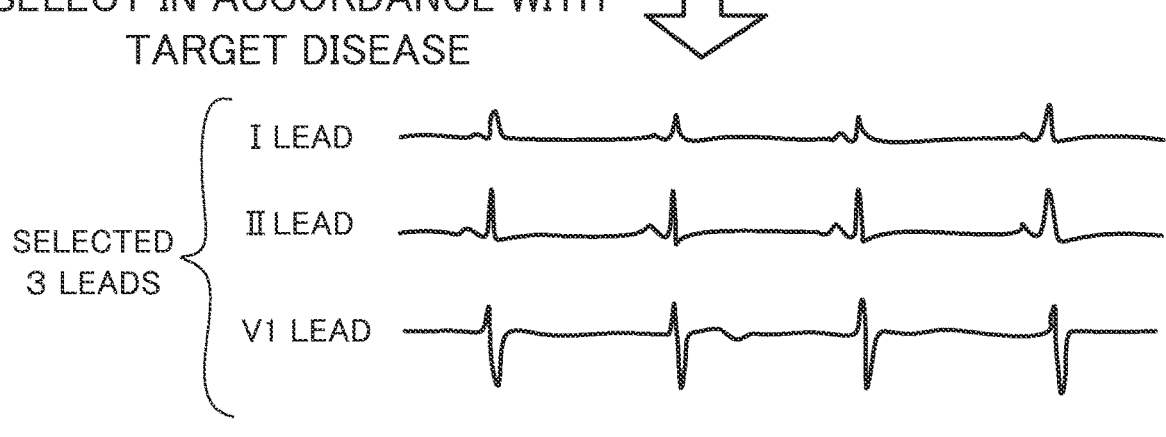

Next, a specific example of the processing executed by the lead data acquisition unit 30, the predetermined partial waveform acquisition unit 31, the attention interval acquisition unit 32, and the integration unit 33 will be described. FIG. 3 shows the lead data selected by the lead data acquisition unit 30 in accordance with the target disease that is atrial fibrillation. The upper part of FIG. 3 shows, as typical examples, waveforms based on lead data as follows: I lead, II lead, III lead, aVR lead, and V1 lead. When each lead data of twelve leads is stored in the training data storage unit 22, the lead data acquisition unit 30 acquires the lead data of I, II, and V1 leads that are effective for evaluating the presence or absence of atrial fibrillation that is the target disease, as shown in the lower part of FIG. 3. After that, from the lead data of I lead, II lead, and V1 lead, the predetermined partial waveform acquisition unit 31 extracts the predetermined partial waveforms and the attention interval acquisition unit 32 and the integration unit 33 extract the regular partial waveforms. Then, the lead data to be inputted to the third model is generated by the integration unit 33.

FIG. 4 is an enlarged view of the waveform of lead data. As an example, the lead data includes two waveforms, one of which is enclosed by a dashed frame. As shown, each waveform includes P wave, Q wave, R wave, S wave, T wave, U wave and the like, and it is possible to detect each position of these waves by signal processing.

Then, the predetermined partial waveform acquisition unit 31 extracts the lead data representing the predetermined partial waveforms from the lead data of the sequential waveform. In this case, examples of the predetermined partial waveforms include the interval (first example of the predetermined partial waveforms in FIG. 4) from the P wave to the Q wave (PQ interval), the interval (second example of the predetermined partial waveform in FIG. 4) from the Q wave to the T wave (QT interval), any other interval between any two waves, an interval (e.g., P wave interval, R wave interval) obtained by cutting off only an individual wave. On the other hand, the attention interval acquisition unit 32 inputs the lead data itself indicating the sequential waveform as input data to the second model.

Figure 5:
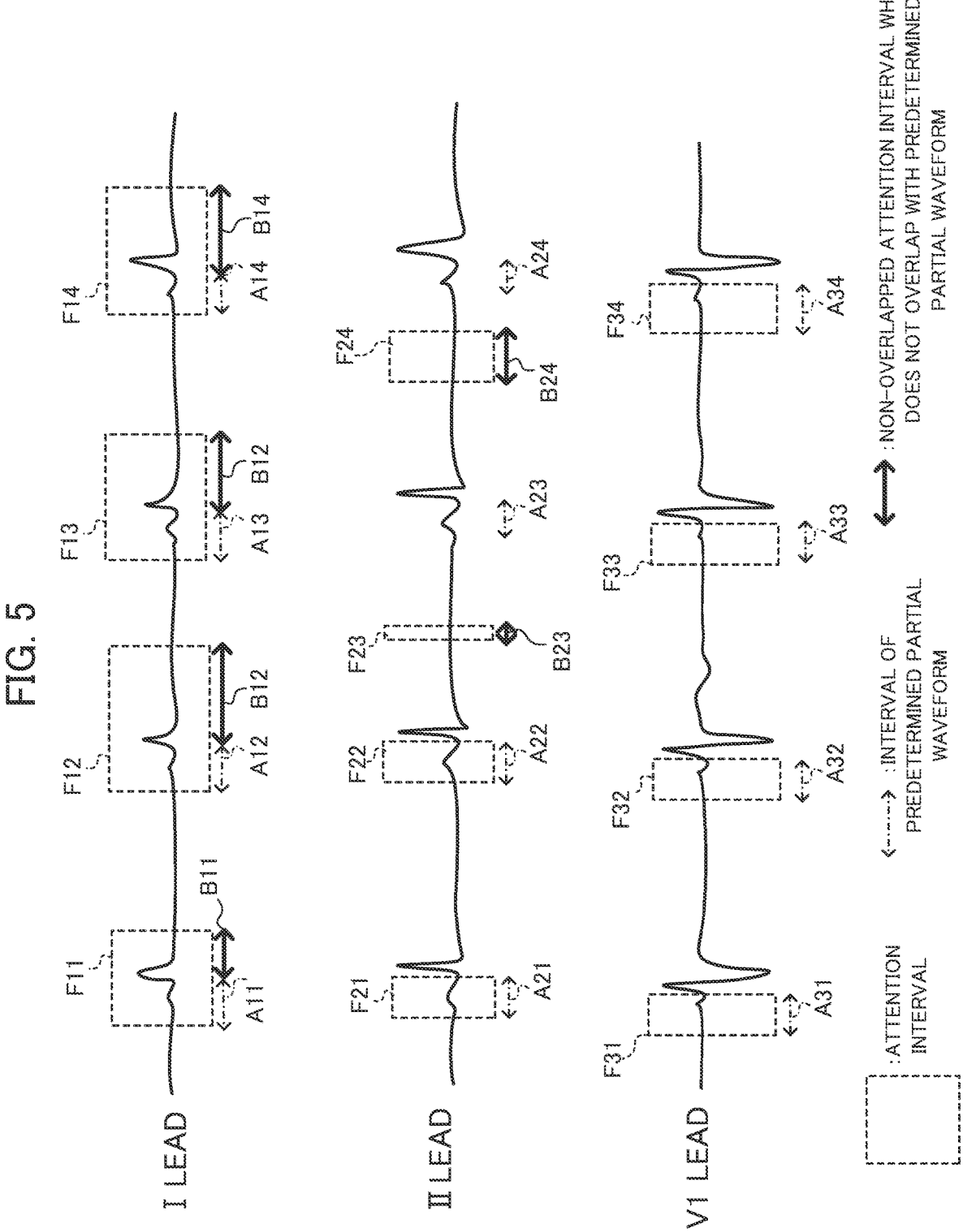
FIG. 5 is a diagram showing the waveforms of the lead I, lead II, and lead V1 which are selected when the target disease is the auricular fibrillation, together with the attention interval.

FIG. 5 is a diagram showing, together with attention intervals, the waveforms indicated by the lead data corresponding to the I, II, and V1 leads selected when the target disease is atrial fibrillation. Here, the attention parts regarding the I lead are indicated by the dashed line frames F11 to F14, the attention parts regarding II lead are indicated by the dashed line frames F21 to F24, and the attention parts regarding V1 lead are indicated by the dashed line frames F31 to F34. For example, the attention intervals are determined to be any intervals where the coefficient outputted by the attention mechanism added to the second model is equal to or more than a predetermined value. Further, in FIG. 5, the intervals corresponding to the predetermined partial waveforms in I lead are indicated by the arrows A11 to A14, the intervals corresponding to the predetermined partial waveforms in II lead are indicated by the arrows A21 to A24, the intervals corresponding to the predetermined partial waveforms in V1 lead are indicated by the arrows A31 to A34, respectively. In this example, the PQ intervals are defined as the intervals corresponding to the predefined partial waveforms in every lead.

Here, regarding the I lead, the attention intervals indicated by the dashed line frames Flt to F14 are present in the respective waveforms, and partially overlap with the predetermined partial waveforms, and have a wider range than the predetermined partial waveforms, respectively. Specifically, each part indicated by the arrows B11 to B14 is an attention interval (also referred to as "non-overlapped attention interval") which does not overlap with the predetermined partial waveform. In this instance, the learning unit 34 extracts each partial waveform (in this case, the vicinity of each QT interval) in which the non-overlapped attention interval is regularly generated as a regular partial waveform in the lead data of I lead.

On the other hand, regarding the II lead, the attention intervals indicated by the dashed line frames F21 to F24 are present in the respective waveforms, and each includes: an interval that matches the predetermined partial waveform; and a non-overlapped attention interval (see arrows B23 to B24) that does not overlap with the predetermined partial waveform. Specifically, the attention intervals indicated by the broken line frames F21 to F22 coincide with the predetermined partial waveforms, and the entire attention intervals indicated by the broken line frames F23 to F24 (i.e., the intervals indicated by the arrow B23 to B24) are non-overlapped attention intervals, respectively. In this instance, the learning unit 34 determines that a non-overlapped attention interval is generated in the vicinity of the U wave by a frequency (50% in this case) equal to or more than a predetermined degree in the lead data of the II lead, and extracts each partial waveform in the vicinity of each U wave as a regular partial waveform.

Regarding the V1 lead, the attention intervals indicated by the dashed line frames F31 to F34 entirely match the predetermined partial wave forms, respectively. Therefore, the learning unit 34 determines that there is no regular partial waveform in the V1 lead.

(4) Processing Flow

Figure 6:
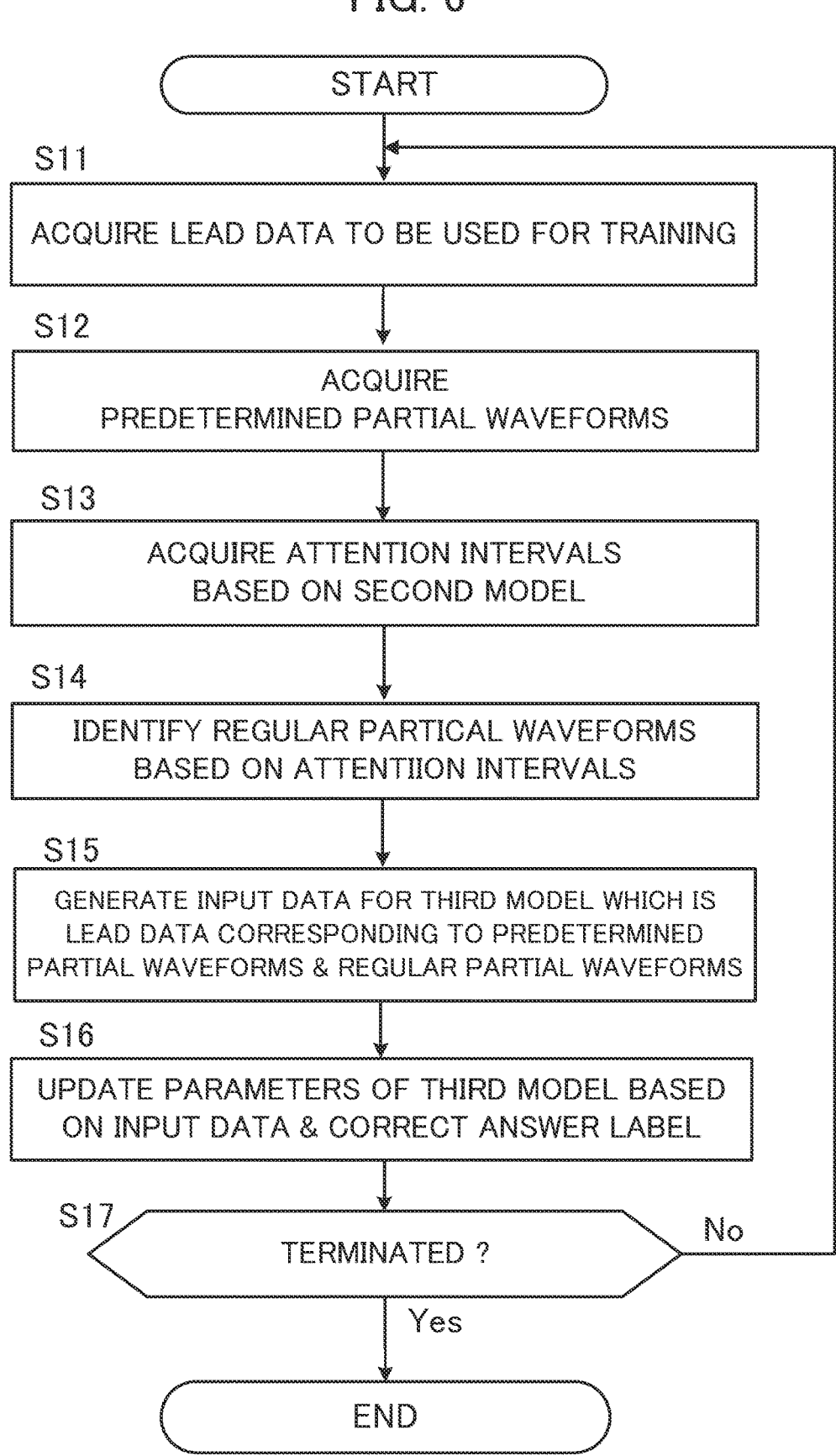
FIG. 6 illustrates an example of a flowchart illustrating an outline of a process executed by the learning device according to the first example embodiment.

FIG. 6 is an example of a flowchart illustrating an outline of process that is executed by the learning device 1 in the first example embodiment.

First, the learning device 1 acquires the lead data to be used for the training of the third model from the training data storage unit 22 (step S11). Next, the learning device 1 acquires the predetermined partial waveforms (step S12). In this instance, the learning device 1 extracts the lead data corresponding to the predetermined partial waveforms from the lead data acquired at step S11.

Then, the learning device 1 acquires the attention intervals based on the second model (step S13). In this case, the learning device 1 extracts, from the lead data acquired at step S11, the lead data corresponding to the attention intervals indicated by the attention interval information outputted by the second model as a result of inputting the lead data acquired at step S11 to the second model. Then, the learning device 1 identifies the regular partial waveforms based on the attention intervals acquired at step S13 (step S14).

Next, the learning device 1 generates the input data to the third model that is the lead data corresponding to the predetermined partial waveforms and the regular partial waveforms (step S15). Then, the learning device 1 updates the parameters of the third model, based on the input data generated at step S15 and the correct answer label corresponding to the lead data acquired at step S11 (step S16).

Then, the learning device 1 determines whether or not to terminate the training of the third model (step S17). For example, the learning device 1 determines that the training of the third model should be terminated, if the processes at step S11 to step S16 are executed for all sets of the lead data and the corresponding correct answer label stored in the training data storage unit 22, if the processes at step S11 to step S16 are executed by a predetermined number of times, or if the loss of the result outputted by the third model at the time of parameter updating is less than a predetermined degree. If it is determined that the training of the third model should be terminated (step S17; Yes), the learning device 1 terminates the process of the flowchart. On the other hand, if the learning device 1 determines that the training of the third model should not be terminated (step S17; No), the learning device 1 gets back to the process at step S11. In this instance, at step S11, the learning device 1 acquires the lead data which has not yet been used for training.

Second Example Embodiment

In the second example embodiment, after acquiring the learned third model in the first example embodiment, the learning device 1 calculates the accuracy index for evaluating the accuracy of each of the first model and the third model, and performs model selection processing for selecting one of the first model and the third model for each target disease. It enables accurate selection of the model to be used for each target disease. Hereinafter, the same elements as those in the first example embodiment are appropriately denoted by the same reference numerals, and a description thereof will be omitted. It is hereinafter assumed that the hardware configuration of the learning device 1 according to the second example embodiment is identical to the configuration shown in FIG. 1.

Figure 7:
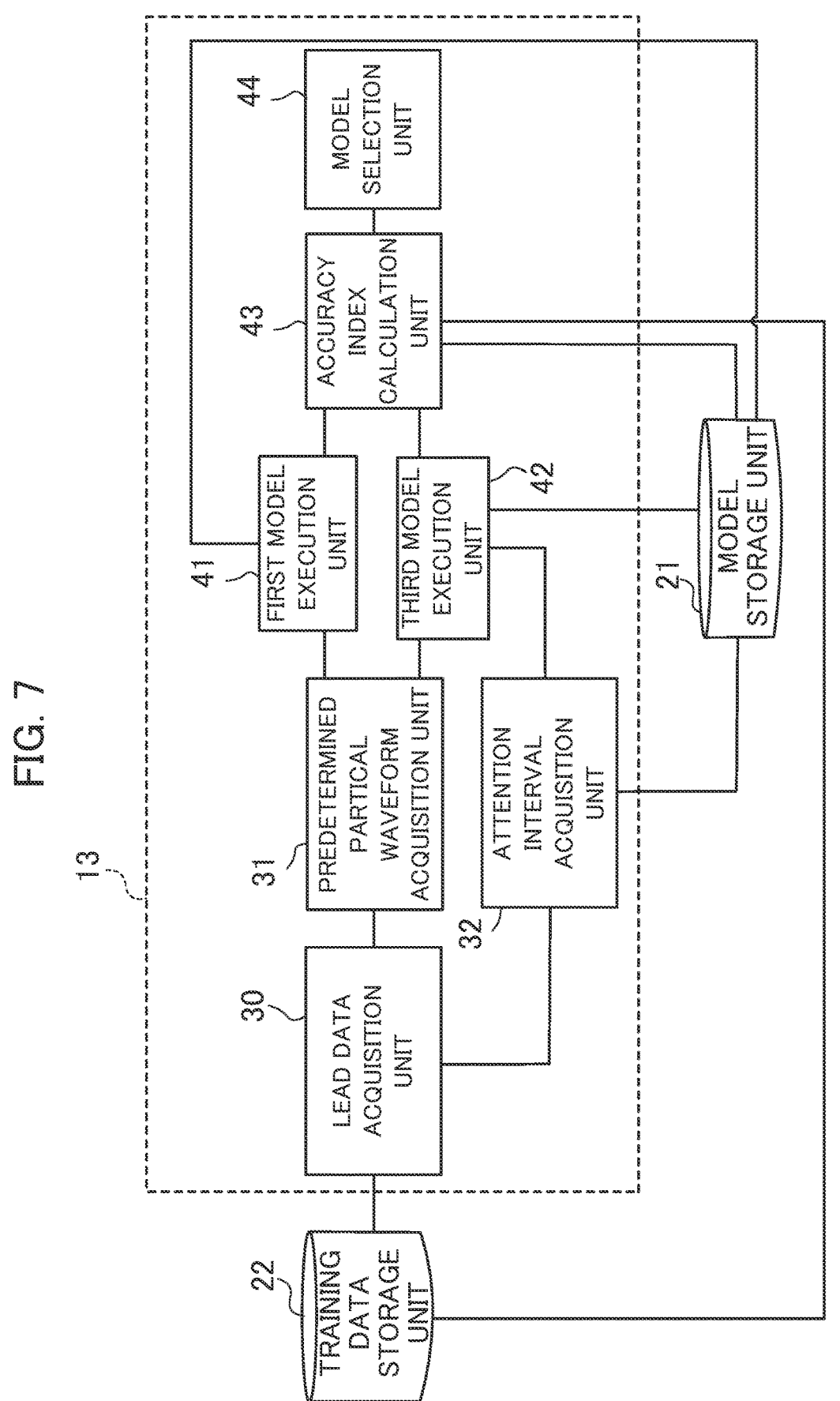
FIG. 7 is a functional block diagram of a learning device in a second example embodiment.

FIG. 7 is a functional block diagram of the learning device 1 according to the second example embodiment. The processor 13 of the learning device 1 according to the second example embodiment functionally includes a lead data acquisition unit 30, a predetermined partial waveform acquisition unit 31, an attention interval acquisition unit 32, a first model execution unit 41, a third model execution unit 42, an accuracy index calculation unit 43, and a model selection unit 44.

The lead data acquisition unit 30 sequentially acquires the lead data of each set from the plurality of sets of lead data and the corresponding correct answer label stored in the training data storage unit 22, and supplies the acquired lead data to the predetermined partial waveform acquisition unit 31 and the attention interval acquisition unit 32. In some embodiments, the training data storage unit 22 stores validation data other than the training data used for the training of the third model, and the lead data acquisition unit 30 sequentially acquires the lead data from the validation data.

The predetermined partial waveform acquisition unit 31 acquires the lead data corresponding to the predetermined partial waveforms from the lead data supplied from the lead data acquisition unit 30, and supplies the acquired lead data to the first model execution unit 41 and the third model execution unit 42. The attention interval acquisition unit 32 acquires the lead data corresponding to the attention intervals based on the second model from the lead data supplied from the lead data acquisition unit 30, and supplies the acquired lead data to the third model execution unit 42.

The first model execution unit 41 executes the first model using the lead data corresponding to the predetermined partial waveforms outputted by the predetermined partial waveform acquisition unit 31 as input data. In this case, the first model execution unit 41 acquires the learned parameters of the first model from the model storage unit 21 and inputs the lead data corresponding to the predetermined partial waveforms to the first model to which the parameters are applied. Then, the first model execution unit 41 supplies the determination result of the presence or absence of the target disease outputted by the first model to the accuracy index calculation unit 43.

The third model execution unit 42 executes the third model on the basis of the lead data corresponding to the predetermined partial waveforms outputted by the predetermined partial waveform acquisition unit 31 and the lead data corresponding to the regular partial waveforms determined on the basis of the attention intervals outputted by the attention interval acquisition unit 32. In this case, first, the third model execution unit 42 identifies the regular partial waveforms from the attention intervals by executing the same process as the integration unit 33 in the first example embodiment. Then, the third model execution unit 42 acquires the learned parameters of the third model from the model storage unit 21, and inputs the lead data corresponding to the regular partial waveforms and the predetermined partial waveforms to the third model to which the above-described parameters are applied. The first model execution unit 41 supplies the determination result of the presence or absence of the target disease outputted by the third model to the accuracy index calculation unit 43.

The accuracy index calculation unit 43 determines the correctness of the determination result outputted by each of the first model and the second model based on the determination result of the presence or absence of the target disease supplied from the first model execution unit 41, the determination result of the presence or absence of the target disease supplied from the third model execution unit 42, and the correct answer label corresponding to the target lead data. Then, the accuracy index calculation unit 43 holds the correctness determination results outputted by the first model and the third model. Then, if correctness determination results regarding all sets of the lead data for validation and the corresponding correct answer label are obtained, the accuracy index calculation unit 43 calculates the accuracy index values regarding the first model and the second model, respectively. The accuracy index to be calculated by the accuracy index calculation unit 43 may be a one or more types of indices, and examples thereof include singularity, sensitivity, and any other accuracy index used for evaluation regarding validation. The accuracy index calculation unit 43 supplies the calculated accuracy index value for each of the first model and the third model to the model selection unit 44.

The model selection unit 44 compares the accuracy index value of the first model with the accuracy index value of the third model, which are supplied from the accuracy index calculation unit 43, and determines which of the first model or the third model to use, based on the comparison result. It should be noted that in general, the accuracy index to be put an emphasis on differs according to the type of the disease to be diagnosed and the operation situation in which the diagnosis is made. Therefore, the model selection unit 44 may determine which of the first model or the third model is to be used, for each application group classified by the type and the operation situation of the target disease. The learning device 1 may acquire information (which may be a weight coefficient for each accuracy index) indicating the weight for each accuracy index for each application from the interface 11, the memory 12, or the input unit 14 and determines which of the first model or the third model is to be used for each application based on the acquired information. Then, the model selection unit 44 outputs information indicating a model to be used for each application. In this case, the model selection unit 44 may store information indicating the weight for each accuracy index for each application in the memory 12, may transmit the information to an external device via the interface 11, or may display information by the output unit 15.

The model selection unit 44 may receive an input that specifies which to use the first model or the third model from a doctor who is the user by the input unit 14. In this case, the model selection unit 44 displays or outputs by audio the accuracy index value of the first model and the accuracy index value of the third model supplied from the accuracy index calculation unit 43 by the output unit 15, thereby to present the accuracy index values of the first model and the third model to the user. In this case, the user compares the accuracy index value of the first model with the accuracy index value of the third model, and performs the input operation of selecting a model by the input unit 14 in accordance with the application to be executed. Thereby, the model selection unit 44 can assist the user to perform decision making as to which of the first model or the third model to use.

Figure 8:
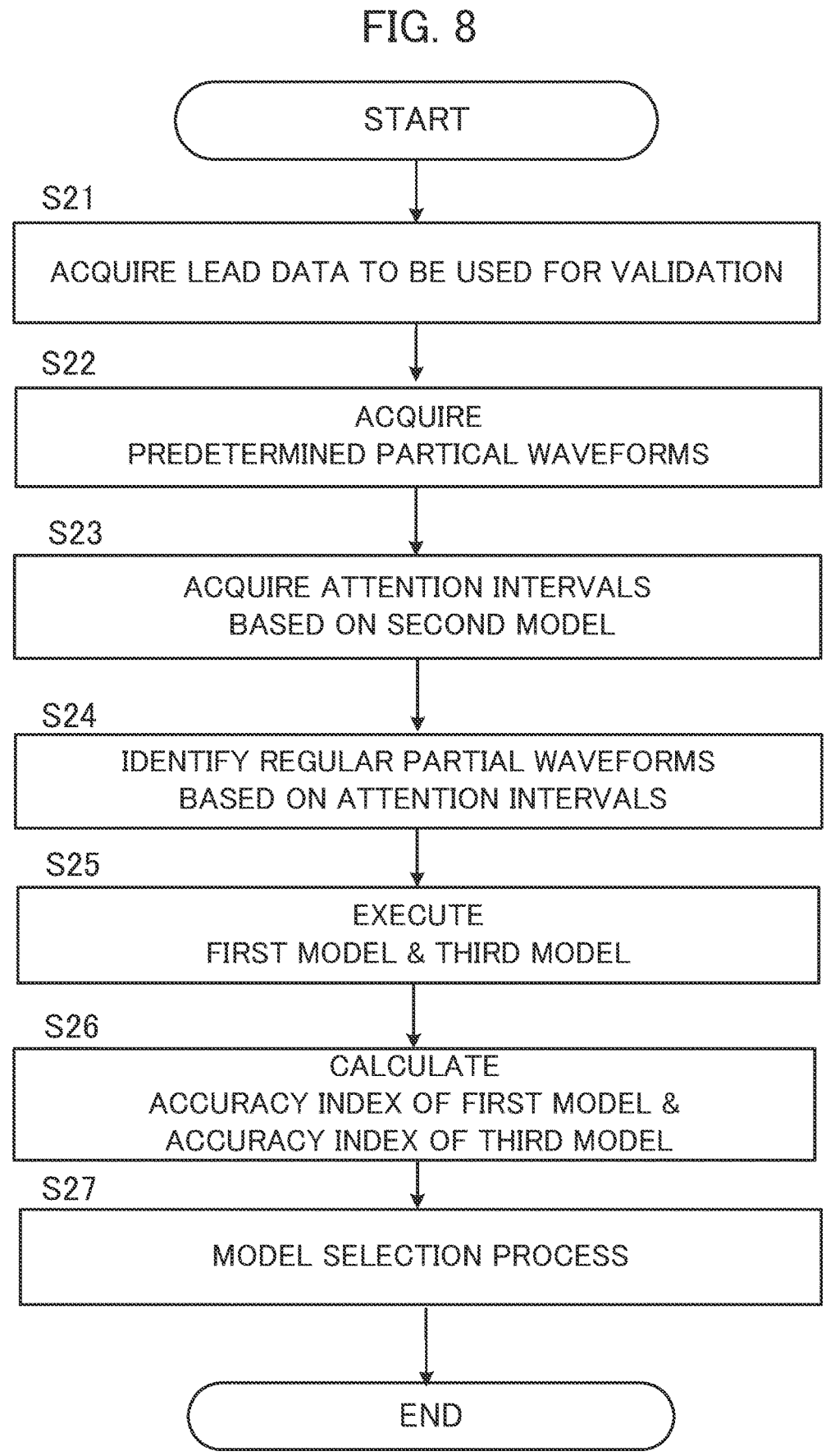
FIG. 8 illustrates an example of a flowchart showing an outline of a process executed by the learning device in the second example embodiment.

FIG. 8 is an example of a flowchart illustrating an outline of processing that is executed by the learning device 1 in the second example embodiment.

First, the learning device 1 acquires the lead data for validation to be used for calculation of the accuracy index from the training data storage unit 22 (step S21). Next, the learning device 1 acquires the predetermined partial waveforms (step S22). In this instance, the learning device 1 extracts the lead data corresponding to the predetermined partial waveforms from the lead data acquired at step S21.

Then, the learning device 1 acquires the attention intervals based on the second model (step S23). In this case, the learning device 1 extracts, from the lead data acquired at step S21, the lead data corresponding to the attention intervals indicated by the attention interval information outputted by the second model as a result of inputting the lead data acquired at step S21 to the second model. Then, the learning device 1 identifies the regular partial waveforms based on the attention intervals acquired at step S23 (step S24).

Then, the learning device 1 executes the first model and the third model, respectively (step S25). In this instance, the learning device 1 executes the first model based on the lead data corresponding to the predetermined partial waveforms acquired at step S22 and executes the third model based on the lead data corresponding to the predetermined partial waveforms acquired at step S22 and the regular partial waveforms identified at step S24.

Then, the learning device 1 calculates the accuracy index values of the first model and the third model, respectively (step S26). In this case, the learning device 1 refers to the correct answer label stored in the training data storage unit 22 and determines the correctness of the determination result for each sample inputted into the first model and the third model at step S25, and calculates the accuracy index value of the first model and the third model, respectively, by aggregating the determination results of the correctness. Then, the learning device 1 performs a model selection process (step S27). In this case, the learning device 1 selects which model is to be used by comparing the calculated accuracy index value of the first model with the calculated accuracy index value of the third model. The learning device 1 may receive an input specifying which of the first model or the third model is to be used from the user by the input unit 14.

Third Example Embodiment

In the third example embodiment, the learning device 1 executes the model selected based on the model selection process for selecting one of the first model and the third model for the target disease according to the second example embodiment. Hereinafter, the same elements as those in the first example embodiment or in the second example embodiment are appropriately denoted by the same reference numerals, and a description thereof will be omitted. It is hereinafter assumed that the hardware configuration of the learning device 1 according to the third example embodiment is identical to the configuration shown in FIG. 1.

FIG. 9 is a functional block diagram of the learning device 1 according to the third example embodiment. The processor 13 of the learning device 1 according to the third example embodiment functionally includes an ECD data acquisition unit 51, an input data generation unit 52, a selected model execution unit 53, and an output control unit 54.

The ECD data acquisition unit 51 acquires the ECD data regarding a target person (e.g., patient) subject to a diagnosis. In other words, the target person is a person who needs to receive a diagnosis of the target disease. The ECD data acquisition unit 51 may acquire the ECD data by receiving the ECD data from any external device through the interface 11 or may acquire the ECD data from the memory 12 which stores the ECD data regarding the target person in advance.

The input data generation unit 52 generates the input data that is lead data of the acquired ECD data to be inputted to the selected model. The selected model is model selected based on the model selection process for selecting one of the first model and the third model for the target disease according to the second example embodiment. If the selected model is the first model, the input data generation unit 52 generates, as the above-mentioned input data, the lead data corresponding to the predetermined partial waveforms. If the selected model is the third model, the input data generation unit 52 generates, as the above-mentioned input data, the lead data corresponding to the predetermined partial waveforms and the regular partial waveforms. It is noted that the input data generation unit 52 generates the above-mentioned predetermined partial waveforms and regular partial waveforms from the lead data of the acquired ECD data in the same way as in the first example embodiment or the second example embodiment.

The selected model execution unit 53 makes a diagnosis of the target disease based on the input data supplied from the input data generation unit 52. In this case, the selected model execution unit 53 builds the selected model with reference to the model storage unit 21 and inputs the input data to the selected model thereby to acquire the diagnosis result (including information regarding presence or absence of the target disease) of the target person outputted from the selected model.

The output control unit 54 controls the output unit 15 to display and/or output, by audio, the diagnosis result supplied from the selected model execution unit 53. Thereby, the output control unit 54 presents the diagnosis result to a healthcare worker (e.g., doctor) which is a user of the learning device 1. In this case, the output control unit 54 may display the sequential waveforms regarding the leads used for the diagnosis and highlight intervals of the sequential waveforms used as the input data which was inputted to the selected model. The intervals used as the input data may be highlighted by dashed frames in such a manner shown in FIG. 5.

According to the third example embodiment, the healthcare worker (e.g., doctor) can make the diagnosis of the target person based on the diagnosis result presented by the learning device 1. This suitably assists the healthcare worker to perform the decision making. Specifically, highlighting intervals of the sequential waveforms used as the input data enables the healthcare worker to recognize the part to be noticed in making the diagnosis. Thereby, it is possible to support the diagnosis by the healthcare worker based on the diagnosis result generated by the learning device 1.

Fourth Example Embodiment

Figure 10:
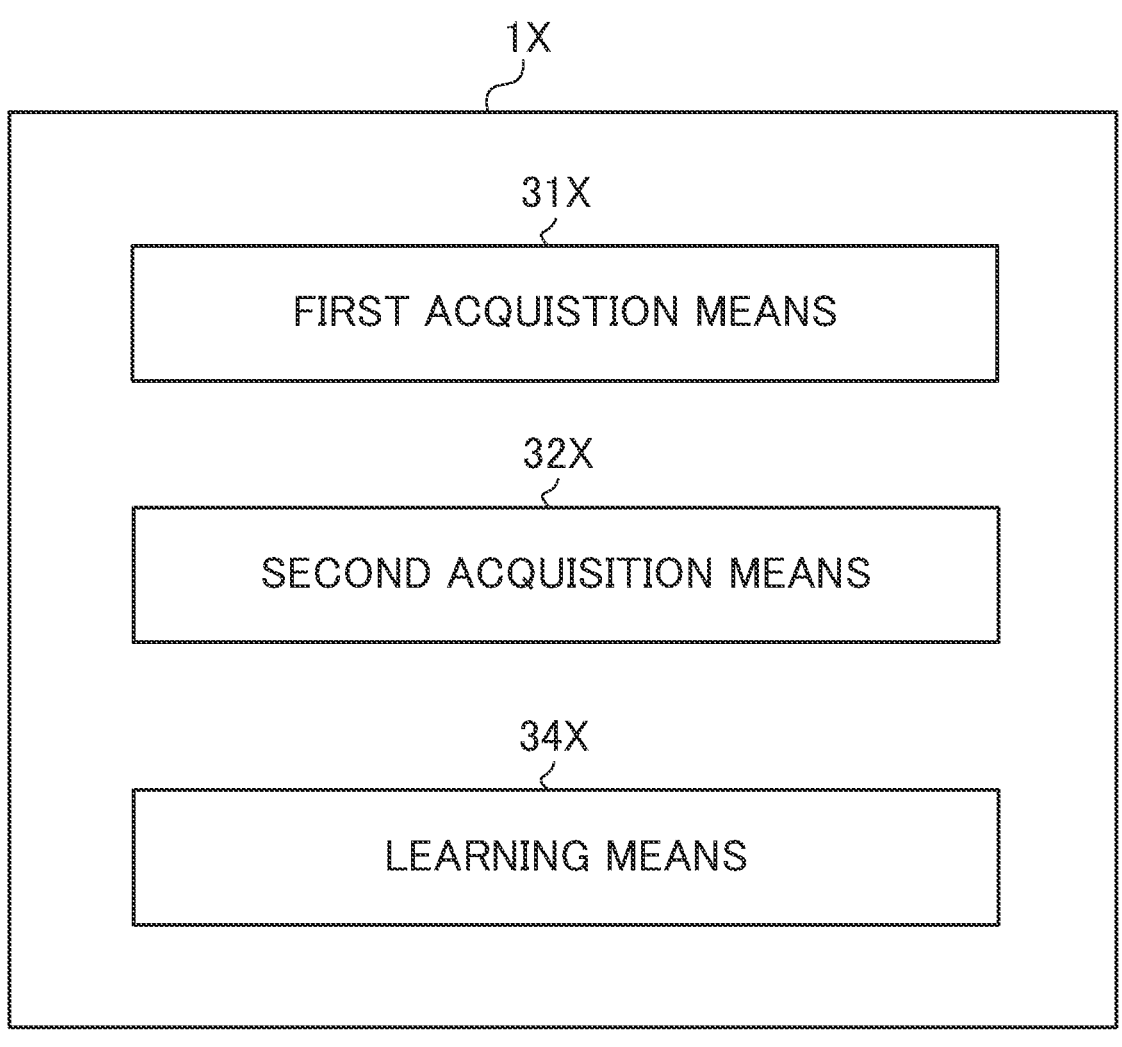
FIG. 10 is a block diagram of a learning device in the fourth example embodiment.

FIG. 10 is a block diagram of a learning device 1X according to a fourth example embodiment. The learning device 1X mainly includes a first acquisition means 31X, a second acquisition means 32X, and a learning means 34X. The learning device 1X may be configured by a plurality of devices.

The first acquisition means 31X is configured to acquire a partial waveform of electrocardiogram data regarding an electrocardiogram of a subject. Examples of the "partial waveform" include the "predetermined partial waveform" according to the first example embodiment. Examples of the first acquisition means 31X include the predetermined partial wave acquisition unit 31 according to the first example embodiment.

The second acquisition means 32X is configured to acquire an attention interval, which is used as a basis for a diagnosis of a target disease, in a sequential waveform of the electrocardiogram data. Examples of the second acquisition means 32X include the attention interval acquisition unit 32 according to the first example embodiment.

The learning means 34X configured to train a model configured to diagnose the target disease, based on the partial waveform and the attention interval. Examples of the "model" include the "third model" according to the first example embodiment. Examples of the learning means 34X include the learning unit 34 according to the first example embodiment.

Figure 11:
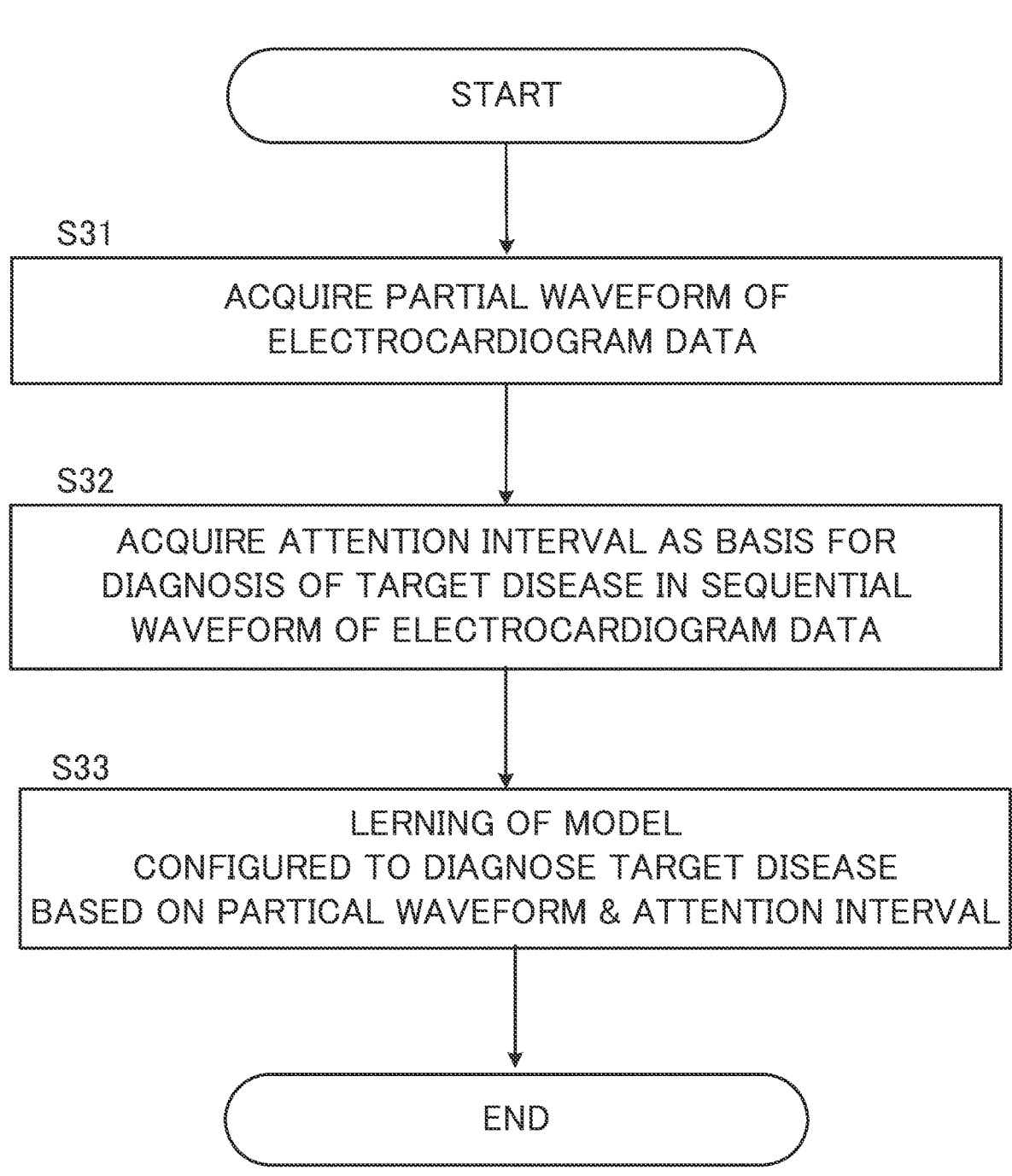
FIG. 11 illustrates an example of a flowchart showing a processing procedure of the learning device in the fourth example embodiment.

FIG. 11 is an exemplary flowchart illustrating a process to be executed by the learning device 1X according to the fourth example embodiment. The first acquisition means 31X acquires a partial waveform of electrocardiogram data regarding an electrocardiogram of a subject (step S31). The second acquisition means 32X acquires an attention interval, which is used as a basis for a diagnosis of a target disease, in a sequential waveform of the electrocardiogram data (step S32). The learning means 34X trains a model configured to diagnose the target disease, based on the partial waveform and the attention interval (step S33).

According to the fourth example embodiment, the learning device 1X can suitably train the model which can diagnose a target disease accurately.

In the example embodiments described above, the program is stored by any type of a non-transitory computer-readable medium (non-transitory computer readable medium) and can be supplied to a control unit or the like that is a computer. The non-transitory computer-readable medium include any type of a tangible storage medium. Examples of the non-transitory computer readable medium include a magnetic storage medium (e.g., a flexible disk, a magnetic tape, a hard disk drive), a magnetic-optical storage medium (e.g., a magnetic optical disk), CD-ROM (Read Only Memory), CD-R, CD-R/W, a solid-state memory (e.g., a mask ROM, a PROM (Programmable ROM), an EPROM (Erasable PROM), a flash ROM, a RAM (Random Access Memory)). The program may also be provided to the computer by any type of a transitory computer readable medium. Examples of the transitory computer readable medium include an electrical signal, an optical signal, and an electromagnetic wave. The transitory computer readable medium can provide the program to the computer through a wired channel such as wires and optical fibers or a wireless channel.

The whole or a part of the example embodiments (including modifications, the same shall apply hereinafter)

described above can be described as, but not limited to, the following Supplementary Notes.

[Supplementary Note 1]

A learning device comprising:

a first acquisition means configured to acquire a partial waveform of electrocardiogram data regarding an electrocardiogram of a subject;

a second acquisition means configured to acquire an attention interval, which is used as a basis for a diagnosis of a target disease, in a sequential waveform of the electrocardiogram data; and a learning means configured to perform a learning of a model configured to diagnose the target disease, based on the partial waveform and the attention interval.

[Supplementary Note 2]

The learning device according to Supplementary Note 1, wherein the partial waveform is a predetermined partial waveform which is a partial waveform predetermined to be specific to the target disease, and wherein the learning means is configured to perform the learning of the model based on the predetermined partial waveform and a regular partial waveform, which is a partial waveform where the attention interval that does not overlap with the predetermined partial waveform appears regularly.

[Supplementary Note 3]

The learning device according to Supplementary Note 2, wherein the model is a model configured to output a diagnosis of the target disease when the electrocardiogram data corresponding to the predetermined partial waveform and the regular partial waveform is inputted to the model.

[Supplementary Note 4]

The learning device according to Supplementary Note 1, wherein the second acquisition means is configured to acquire the attention interval, based on a second model configured to output the diagnosis of the target disease and the attention interval when the electrocardiogram data corresponding to the sequential waveform is inputted to the second model.

[Supplementary Note 5]

The learning device according to Supplementary Note 4, wherein the learning means is configured to train the model, based on attention interval outputted by the second model when the diagnosis of the target disease is correct.

[Supplementary Note 6]

The learning device according to Supplementary Note 3, further comprising an accuracy evaluation calculation means configured to calculate, based on electrocardiogram validation data which is different from the electrocardiogram data, an evaluation index regarding an accuracy of a third model that is the model and the evaluation index regarding an accuracy of a first model that is a model configured to output the diagnosis of the target disease when the electrocardiogram data corresponding to the predetermined partial waveform is inputted thereto.

[Supplementary Note 7]

The learning device according to Supplementary Note 6, further comprising a model selection means configured to select a model to be used for the target disease based on the evaluation index of the third model and the evaluation index of the first model.

[Supplementary Note 8]

The learning method comprising:

acquiring a partial waveform of electrocardiogram data regarding an electrocardiogram of a subject;

acquiring an attention interval, which is used as a basis for a diagnosis of a target disease, in a sequential waveform of the electrocardiogram data; and performing a learning of a model configured to diagnose the target disease, based on the partial waveform and the attention interval.

[Supplementary Note 9]

A non-transitory computer readable storage medium storing a program executed by a computer, the program causing the computer to:

acquire a partial waveform of electrocardiogram data regarding an electrocardiogram of a subject;

acquire an attention interval, which is used as a basis for a diagnosis of a target disease, in a sequential waveform of the electrocardiogram data; and perform a learning of a model configured to diagnose the target disease, based on the partial waveform and the attention interval.

While the invention has been particularly shown and described with reference to example embodiments thereof, the invention is not limited to these example embodiments. It will be understood by those of ordinary skilled in the art that various changes in form and details may be made therein without departing from the spirit and scope of the present invention as defined by the claims. In other words, it is needless to say that the present invention includes various modifications that could be made by a person skilled in the art according to the entire disclosure including the scope of the claims, and the technical philosophy. Each example embodiment can be appropriately combined with other example embodiments. All Patent and Non-Patent Literatures mentioned in this specification are incorporated by reference in its entirety.

DESCRIPTION OF REFERENCE NUMERALS

1, 1X learning device
11 Interface
12 Memory
13 Processor
14 Input unit
15 Output unit
21 Model storage unit
22 Training data storage unit

What is claimed is:

1. An electrocardiogram-based diagnosis model learning device comprising:

at least one memory configured to store instructions; and at least one processor configured to execute the instructions to:

extract, based on data of a continuous waveform of overall lead data, an attention interval of electrocardiogram data by using a second model constituted by a convolutional neural network, wherein the second model, in a case where a diagnosis result is outputted based on the electrocardiogram data, generates the attention interval as an output of an intermediate layer, and wherein the attention interval is a section in which coefficients are equal to or greater than a predetermined value, and is output by an attention mechanism that is added to the second model so that the output in front of full connection is inputted to the attention mechanism;

acquire lead data for validation to calculate an accuracy index from training data, the lead data including P waves, Q waves, R waves, S waves, T waves, and U waves of an electrocardiogram waveform;

acquire a predetermined partial waveform of electrocardiogram data regarding an electrocardiogram of a subject, the predetermined partial waveform being predetermined to be specific to a target disease;

extract the lead data corresponding to the predetermined partial waveform from the lead data;

in a case where the diagnosis result output by the second model for input lead data matches ground-truth label of the input lead data, perform machine learning of a third machine learning model configured to diagnose the target disease, based on the predetermined partial waveform and a regular partial waveform, each corresponding to the input lead data, which is a partial waveform where the attention interval that does not overlap with the predetermined partial waveform appears regularly, wherein the third machine learning model is configured to output the diagnosis result of the target disease when the electrocardiogram data corresponding to the predetermined partial waveform and the regular partial waveform is inputted to the third machine learning model; and calculate, based on electrocardiogram validation data which is different from the electrocardiogram data, an evaluation index regarding an accuracy of the third machine learning model, wherein the evaluation index relates to an accuracy of a first model that is a model configured to output the diagnosis result of the target disease when the electrocardiogram data corresponding to the predetermined partial waveform is inputted thereto.

2. The electrocardiogram-based diagnosis model learning device according to claim 1, wherein the at least one processor is configured to execute the instructions to acquire the attention interval, based on the second model configured to output the diagnosis result of the target disease and the attention interval when the electrocardiogram data corresponding to a sequential waveform is inputted to the second model.

3. The electrocardiogram-based diagnosis model learning device according to claim 2, wherein the at least one processor is configured to execute the instructions to perform the machine learning of the third machine learning model, based on attention interval outputted by the second model when the diagnosis result of the target disease is correct.

4. The electrocardiogram-based diagnosis model learning device according to claim 1, wherein the at least one processor is configured to further execute the instructions to select a model to be used for the target disease based on the evaluation index regarding an accuracy of the third machine learning model and the evaluation index regarding an accuracy of the first model.

5. The electrocardiogram-based diagnosis model learning device according to claim 4, wherein the at least one processor is configured to further execute the instructions to:

acquire the electrocardiogram data regarding a target person to be diagnosed;

if the selected model is the first model, generate the predetermined partial waveform based on the acquired electrocardiogram data regarding the target person, and input the predetermined partial waveform to the first model thereby to output the diagnosis result of the target disease; and if the selected model is the third machine learning model, generate the predetermined partial waveform and the regular partial waveform based on the acquired electrocardiogram data regarding the target person, and input the predetermined partial waveform and the regular partial waveform to the third machine learning model thereby to output the diagnosis result of the target disease.

6. The electrocardiogram-based diagnosis model learning device according to claim 5, wherein the at least one processor is configured to execute the instructions to display the diagnosis result on a display device to assist a healthcare worker to perform a decision making.

7. An electrocardiogram-based diagnosis model learning method executed by a computer, comprising:

extracting, based on data of a continuous waveform of overall lead data, an attention interval of electrocardiogram data by using a second model constituted by a convolutional neural network, wherein the second model, in a case where a diagnosis result is outputted based on the electrocardiogram data, generates the attention interval as an output of an intermediate layer, and wherein the attention interval is a section in which coefficients are equal to or greater than a predetermined value, and is output by an attention mechanism that is added to the second model so that the output in front of full connection is inputted to the attention mechanism;

acquiring lead data for validation to calculate an accuracy index from training data, the lead data including P waves, Q waves, R waves, S waves, T waves, and U waves of an electrocardiogram waveform;

acquiring a predetermined partial waveform of electrocardiogram data regarding an electrocardiogram of a subject, the predetermined partial waveform being predetermined to be specific to a target disease;

extracting the lead data corresponding to the predetermined partial waveform from the lead data;

in a case where the diagnosis result output by the second model for input lead data matches ground-truth label of the input lead data, performing machine learning of a third machine learning model configured to diagnose the target disease, based on the predetermined partial waveform and a regular partial waveform, each corresponding to the input lead data, which is a partial waveform where the attention interval that does not overlap with the predetermined partial waveform appears regularly, the third machine learning model outputting the diagnosis result of the target disease when the electrocardiogram data corresponding to the predetermined partial waveform and the regular partial waveform is inputted to the third machine learning model; and calculating, based on electrocardiogram validation data which is different from the electrocardiogram data, an evaluation index regarding an accuracy of the third machine learning model, wherein the evaluation index relates to an accuracy of a first model that is a model configured to output the diagnosis result of the target disease when the electrocardiogram data corresponding to the predetermined partial waveform is inputted thereto.

8. A non-transitory computer readable storage medium storing a program executed by a computer, the program causing the computer to:

extract, based on data of a continuous waveform of overall lead data, an attention interval of electrocardiogram data by using a second model constituted by a convolutional neural network, wherein the second model, in a case where a diagnosis result is outputted based on the electrocardiogram data, generates the attention interval as an output of an intermediate layer, and wherein the attention interval is a section in which coefficients are equal to or greater than a predetermined value, and is output by an attention mechanism that is added to the second model so that the output in front of full connection is inputted to the attention mechanism;

acquire lead data for validation to calculate an accuracy index from training data, the lead data including P waves, Q waves, R waves, S waves, T waves, and U waves of an electrocardiogram waveform;

acquire a predetermined partial waveform of electrocardiogram data regarding an electrocardiogram of a subject, the predetermined partial waveform being predetermined to be specific to a target disease;

extract the lead data corresponding to the predetermined partial waveform from the lead data;

in a case where the diagnosis result output by the second model for input lead data matches ground-truth label of the input lead data, perform machine learning of a third machine learning model configured to diagnose the target disease, based on the predetermined partial waveform and a regular partial waveform, each corresponding to the input lead data, which is a partial waveform where the attention interval that does not overlap with the predetermined partial waveform appears regularly, the third machine learning model being configured to output the diagnosis result of the target disease when the electrocardiogram data corresponding to the predetermined partial waveform and the regular partial waveform is inputted to the third machine learning model; and calculate, based on electrocardiogram validation data which is different from the electrocardiogram data, an evaluation index regarding an accuracy of the third machine learning model, wherein the evaluation index relates to an accuracy of a first model that is a model configured to output the diagnosis result of the target disease when the electrocardiogram data corresponding to the predetermined partial waveform is inputted thereto.

* * * * *